(12) United States Patent
Cash et al.

(10) Patent No.: US 8,671,741 B2
(45) Date of Patent: Mar. 18, 2014

(54) EXTENDABLE MOISTURE CONTENT SENSING SYSTEM

(75) Inventors: Michael Cash, Mountain View, CA (US); D'Anne Beukelaur Hanks, Santa Rosa, CA (US); Arthur F. Lange, Sunnyvale, CA (US); Brian Jackman, Concord, CA (US); Brian A. Jackson, San Francisco, CA (US)

(73) Assignee: Trimble Navigation Limited, Sunnyvale, CA (US)

( * ) Notice: Subject to any disclaimer, the term of this patent is extended or adjusted under 35 U.S.C. 154(b) by 295 days.

(21) Appl. No.: 13/172,716

(22) Filed: Jun. 29, 2011

(65) Prior Publication Data
US 2013/0000393 A1 Jan. 3, 2013

(51) Int. Cl.
*G01N 25/56* (2006.01)

(52) U.S. Cl.
USPC .......... 73/73; 73/29.01; 73/29.05; 73/335.04; 324/667; 702/97

(58) Field of Classification Search
USPC .......... 33/679.1, 712; 324/667; 73/29.02, 73/29.05, 335.01–335.04, 73; 702/97; 248/542
See application file for complete search history.

(56) References Cited

U.S. PATENT DOCUMENTS

| | | |
|---|---|---|
| 5,003,329 A | 3/1991 | Habashi |
| 5,087,916 A | 2/1992 | Metzdorff et al. |
| 5,103,250 A | 4/1992 | Arifuku et al. |
| 5,247,356 A | 9/1993 | Ciampa |
| 5,427,356 A | 6/1995 | Krotov et al. |
| 5,506,644 A | 4/1996 | Suzuki et al. |
| 5,517,419 A | 5/1996 | Lanckton et al. |
| 5,581,299 A | 12/1996 | Raney |
| 5,596,494 A | 1/1997 | Kuo |
| 5,633,946 A | 5/1997 | Lachinski et al. |
| 5,646,207 A | 7/1997 | Schell |
| 5,689,742 A | 11/1997 | Chamberlain |
| 5,719,773 A | 2/1998 | Choate |
| 5,768,640 A | 6/1998 | Takahashi et al. |
| 5,845,161 A | 12/1998 | Schrock et al. |
| 5,897,728 A | 4/1999 | Cole et al. |
| 5,902,347 A | 5/1999 | Backman et al. |
| 5,913,078 A | 6/1999 | Kimura et al. |

(Continued)

FOREIGN PATENT DOCUMENTS

JP 2007024859 A 2/2007

OTHER PUBLICATIONS

Werne&Thiel sensortechnic, "Equipment Description: Arnold moisture measuring probes Type FS(x)", http://www.werne-thiel.de/pdf/download30.pdf, Jan. 19, 2007, Accessed Jan. 22, 2010.*

(Continued)

*Primary Examiner* — Hezron E Williams
*Assistant Examiner* — Alexander Mercado

(57) ABSTRACT

A moisture content sensing system is described comprising a collar mechanically coupled with a clean grain transport system. An extendable support extends through the collar and has an extendable capacitive sensor element disposed at one end. The extendable support is configured to be located at a first position in which the extendable capacitive sensor element is disposed adjacent to clean grain conveyed by the clean grain transport system and moved to a second position wherein the extendable capacitive sensor element is disposed at least partially within the clean grain of the clean grain transport system.

19 Claims, 14 Drawing Sheets

(56) References Cited

U.S. PATENT DOCUMENTS

| | | | |
|---|---|---|---|
| 5,922,939 A * | 7/1999 | Cota | 73/29.01 |
| 5,966,122 A | 10/1999 | Itoh | |
| 5,969,243 A * | 10/1999 | Frey et al. | 73/335.04 |
| 5,991,690 A | 11/1999 | Murphy | |
| 6,009,359 A | 12/1999 | El-Hakim et al. | |
| 6,070,682 A | 6/2000 | Isogai et al. | |
| 6,076,917 A | 6/2000 | Wen | |
| 6,085,135 A | 7/2000 | Steckel | |
| 6,128,446 A | 10/2000 | Schrock et al. | |
| 6,141,614 A | 10/2000 | Janzen et al. | |
| 6,185,990 B1 * | 2/2001 | Missotten et al. | 73/73 |
| 6,205,397 B1 | 3/2001 | Eslambolchi et al. | |
| 6,222,985 B1 | 4/2001 | Miyake et al. | |
| 6,282,362 B1 | 8/2001 | Murphy et al. | |
| 6,337,951 B1 | 1/2002 | Nakamura | |
| 6,346,980 B1 | 2/2002 | Tani et al. | |
| 6,401,069 B1 | 6/2002 | Boys et al. | |
| 6,504,571 B1 | 1/2003 | Narayanaswami et al. | |
| 6,574,561 B2 | 6/2003 | Alexander et al. | |
| 6,597,818 B2 | 7/2003 | Kumar et al. | |
| 6,690,883 B2 | 2/2004 | Pelletier | |
| 6,691,135 B2 | 2/2004 | Pickett et al. | |
| 6,732,162 B1 | 5/2004 | Wood et al. | |
| 6,741,948 B2 | 5/2004 | Hauger et al. | |
| 6,802,205 B2 * | 10/2004 | Barguirdjian et al. | 73/73 |
| 6,868,340 B2 | 3/2005 | Alexander et al. | |
| 6,917,206 B2 | 7/2005 | Rains et al. | |
| 6,975,942 B2 | 12/2005 | Young et al. | |
| 6,993,196 B2 | 1/2006 | Sun et al. | |
| 7,106,328 B2 | 9/2006 | Royan | |
| 7,167,187 B2 | 1/2007 | Scott et al. | |
| 7,191,056 B2 | 3/2007 | Costello et al. | |
| 7,234,106 B2 | 6/2007 | Simske | |
| 7,248,285 B2 | 7/2007 | Needham | |
| 7,248,968 B2 | 7/2007 | Reid | |
| 7,254,485 B2 | 8/2007 | Rooney et al. | |
| 7,283,975 B2 | 10/2007 | Broughton | |
| 7,313,604 B2 | 12/2007 | Wood et al. | |
| 7,411,493 B2 | 8/2008 | Smith | |
| 7,447,613 B2 | 11/2008 | Mertins et al. | |
| 7,465,323 B2 | 12/2008 | Au et al. | |
| 7,466,244 B2 | 12/2008 | Kimchi et al. | |
| 7,482,973 B2 | 1/2009 | Tucker et al. | |
| 7,508,840 B2 | 3/2009 | Delaney | |
| 7,516,563 B2 | 4/2009 | Koch | |
| 7,541,975 B2 | 6/2009 | Sever et al. | |
| 7,617,246 B2 | 11/2009 | Koch et al. | |
| 7,634,380 B2 | 12/2009 | Martin et al. | |
| 7,658,096 B2 * | 2/2010 | Pinto et al. | 73/73 |
| 7,664,233 B1 | 2/2010 | Kirchmeier et al. | |
| 7,720,703 B1 | 5/2010 | Broughton | |
| 7,724,130 B2 | 5/2010 | Norstrom et al. | |
| 7,739,138 B2 | 6/2010 | Chauhan et al. | |
| 7,766,547 B2 * | 8/2010 | Weppenaar et al. | 374/208 |
| 7,813,741 B2 | 10/2010 | Hendrey et al. | |
| 7,836,760 B2 | 11/2010 | Saylor | |
| 7,848,865 B2 | 12/2010 | Di Federico et al. | |
| 7,872,669 B2 | 1/2011 | Darrell et al. | |
| 7,974,853 B1 | 7/2011 | Zimmerman | |
| 8,105,720 B2 | 1/2012 | Koenig et al. | |
| 8,131,118 B1 | 3/2012 | Jing et al. | |
| 8,265,835 B2 | 9/2012 | Peterson et al. | |
| 2002/0055902 A1 | 5/2002 | Faeth | |
| 2002/0120424 A1 | 8/2002 | Hauger et al. | |
| 2003/0182260 A1 | 9/2003 | Pickett et al. | |
| 2003/0187560 A1 | 10/2003 | Keller et al. | |
| 2004/0100285 A1 * | 5/2004 | Rains et al. | 324/664 |
| 2004/0168148 A1 | 8/2004 | Goncalves et al. | |
| 2004/0203571 A1 | 10/2004 | Hashizume | |
| 2004/0225444 A1 | 11/2004 | Young et al. | |
| 2005/0034062 A1 | 2/2005 | Bufkin et al. | |
| 2005/0192752 A1 | 9/2005 | Rooney et al. | |
| 2005/0203671 A1 | 9/2005 | Mertins et al. | |
| 2005/0209815 A1 | 9/2005 | Russon et al. | |
| 2005/0223337 A1 | 10/2005 | Wheeler et al. | |
| 2005/0273300 A1 | 12/2005 | Patwardhan et al. | |
| 2006/0015374 A1 | 1/2006 | Ochs et al. | |
| 2006/0061595 A1 | 3/2006 | Goede et al. | |
| 2006/0095207 A1 | 5/2006 | Reid | |
| 2006/0217105 A1 | 9/2006 | Kumar | |
| 2007/0010924 A1 | 1/2007 | Otani et al. | |
| 2007/0076920 A1 | 4/2007 | Ofek | |
| 2008/0125920 A1 | 5/2008 | Miles et al. | |
| 2008/0140431 A1 | 6/2008 | Anderson et al. | |
| 2008/0191054 A1 | 8/2008 | Di Federico et al. | |
| 2008/0258881 A1 | 10/2008 | Manson et al. | |
| 2008/0258967 A1 | 10/2008 | Manson et al. | |
| 2008/0261627 A1 | 10/2008 | Manson et al. | |
| 2008/0262727 A1 | 10/2008 | Manson et al. | |
| 2008/0262733 A1 | 10/2008 | Manson et al. | |
| 2008/0262734 A1 | 10/2008 | Manson et al. | |
| 2008/0263097 A1 | 10/2008 | Manson et al. | |
| 2008/0263174 A1 | 10/2008 | Manson et al. | |
| 2008/0284587 A1 | 11/2008 | Saigh et al. | |
| 2009/0105969 A1 | 4/2009 | Saylor | |
| 2009/0132132 A1 | 5/2009 | Peterson et al. | |
| 2009/0136788 A1 * | 5/2009 | Koenig et al. | 429/13 |
| 2010/0250136 A1 | 9/2010 | Chen | |
| 2010/0274657 A1 | 10/2010 | Workman et al. | |
| 2010/0277185 A1 * | 11/2010 | Hughes | 324/664 |
| 2010/0306012 A1 | 12/2010 | Zyskowski et al. | |
| 2011/0064312 A1 | 3/2011 | Janky et al. | |
| 2011/0181610 A1 | 7/2011 | Baggs et al. | |
| 2011/0282578 A1 | 11/2011 | Miksa et al. | |
| 2012/0255354 A1 * | 10/2012 | Fu et al. | 73/335.04 |

OTHER PUBLICATIONS

Pawelka, Elizabeth "Make your 3270 applications accessible from PDAs and cell phones", *CCR2: A Publication for the IBM System z Software Community, Issue 6.*, (2008),6 pages.

Luhmann, T. et al., "Close Range Photogrammetry", *Whittles Publishing*, ISBN 0-470-10633-6, (2006).

Gruen, Armin et al., "Algorithms for Automated Extraction of Man-Made Objects from Raster Image Data in a GIS", *Institute of Geodesy & Photogrammetry, Swiss Federal Institute of Technology*, 1 page.

"UpNext: 3D Local Search and Community.", www.upnext.com, (2009).

"You City", www.youcity.com, (2009).

Agrios, Bronwyn et al., "Get in Touch with Volunteered Geographic Information", *ArcUser* www.esri.com, (Summer 2010),50-55.

Qtaishat, K. S., "Assessing the Performance of Different Direct-Georeferencing Strategies", *Institute of Engineering Surveying and Space Geodesy, University of Nottingham*, ASPRS 2006 Annual Congference, Reno, NV,(May 2006),9 pages.

Schwarz, Klaus-Peter "Aircraft Position and Attitude Determination by GPS and INS", *International Archives of Photogrammetry and Remote Sensing, vol. XXXI, Part B6*, Vienna., (1996),7 pages.

Mostafa, Mohamed M., "Digital Image Georeferencing From a Multiple Camera Source by GNS/INS", *ISPRS Journal of Photogrammetry and Remote Sensing*, vol. 56, Issue 1, (Jun. 2001),12 pages.

U.S. Appl. No. 13/023,411, filed Feb. 8, 2011, Weustefeld et al.

U.S. Appl. No. 12/902,013, filed Oct. 11, 2010, Hamilton et al.

Saha, S. K., "Water and Wind Induced Soil Erosion Assessment and Monitoring Using Remote Sensing and GIS", Proceedings of a Training Workshop, Dehra Dun, India, Jul. 7-11, 2003, 315-330.

* cited by examiner

700

```
┌─────────────────────────────────────────────────────┐
│ RECEIVING AN INDICATION OF A DISTANCE AN EXTENDABLE │
│ CAPACITIVE SENSOR ELEMENT EXTENDS INTO A COLLECTION │
│              OF A HARVESTED CROP                    │
│                      710                            │
└─────────────────────────────────────────────────────┘
                         │
                         ▼
┌─────────────────────────────────────────────────────┐
│             RECEIVING A FREQUENCY SIGNAL            │
│                        720                          │
└─────────────────────────────────────────────────────┘
                         │
                         ▼
┌─────────────────────────────────────────────────────┐
│ DETERMINING A MOISTURE CONTENT OF THE HARVESTED CROP│
│ BASED UPON THE INDICATION OF THE DISTANCE AND THE   │
│                 FREQUENCY SIGNAL                    │
│                        730                          │
└─────────────────────────────────────────────────────┘
```

GENERATING AT LEAST ONE DATA TABLE INDICATING A CORRECTION TO A MOISTURE CONTENT READING OF A CONTROLLED MOISTURE CONTENT MATERIAL GENERATED BY AN EXTENDABLE CAPACITIVE SENSOR ELEMENT DISPOSED UPON AN EXTENDABLE SUPPORT
810

RECEIVING AN INDICATION OF A DISTANCE THE EXTENDABLE CAPACITIVE SENSOR ELEMENT EXTENDS INTO A COLLECTION OF CLEAN GRAIN
820

RECEIVING A FREQUENCY SIGNAL
830

DETERMINING A MOISTURE CONTENT OF THE COLLECTION OF CLEAN GRAIN BASED UPON THE INDICATION OF THE DISTANCE AND THE FREQUENCY SIGNAL
840

RETRACTABLY EXTENDING AN EXTENDABLE CAPACITIVE
SENSOR ELEMENT INTO A COLLECTION OF CLEAN GRAIN
WITHIN A CLEAN GRAIN TRANSPORT SYSTEM OF A COMBINE
910

BASED ON A DISTANCE THE EXTENDABLE CAPACITIVE SENSOR
ELEMENT EXTENDS INTO THE COLLECTION OF CLEAN GRAIN
AND A FREQUENCY SIGNAL RECEIVED FROM THE EXTENDABLE
CAPACITIVE SENSOR ELEMENT, DETERMINING A MOISTURE
CONTENT OF THE COLLECTION OF CLEAN GRAIN
920

FIG. 9

EXTENDABLE MOISTURE CONTENT SENSING SYSTEM

BACKGROUND

Yield monitoring is an increasingly important aspect of precision agriculture in which farmers collect and process data pertaining to all aspects of farm operations such as fertilization, pest control, planting, soil conditions, rainfall, crop yields, and locations of various activities. Yield monitoring refers to operations which sense the mass flow of grain being harvested as well as the moisture content of the grain. When this data is correlated with GNSS position data, a farmer can derive an accurate assessment of varying crop yield from field to field, or within the same field.

Grain moisture is important for several reasons. More specifically, the moisture content of the grain affects decisions pertaining to the harvesting, drying, and storage of grain, both at the farm and at grain elevators. Thus, by monitoring the moisture content of the grain, a farmer can derive a better estimate of the actual yield of marketable grain. Furthermore, the farmer can decide whether to store the grain at the farm, whether to dry the grain, or whether to deliver to a grain elevator. Furthermore, the moisture content of the grain affects its selling price. In another example, a farmer is paid for grain having a defined moisture content (e.g., 12%). If the moisture content of the grain is above 12%, the selling price of the grain decreases. Thus, it is convenient, and increasingly important, for a farmer to have a precise measurement of the moisture content of harvested crops.

BRIEF DESCRIPTION OF THE DRAWINGS

The accompanying drawings, which are incorporated in and form a part of this application, illustrate embodiments of the subject matter, and together with the description of embodiments, serve to explain the principles of the embodiments of the subject matter. Unless noted, the drawings referred to in this brief description of drawings should be understood as not being drawn to scale.

FIG. 7 is a flowchart of a method of determining the moisture content of a harvested crop in accordance with one or more embodiments.

FIG. 8 is a flowchart of a method of determining the moisture content of a harvested crop in accordance with one or more embodiments.

FIG. 9 is a flowchart of a method for measuring moisture content of a harvested crop in accordance with various embodiments.

DESCRIPTION OF EMBODIMENTS

Reference will now be made in detail to various embodiments, examples of which are illustrated in the accompanying drawings. While the subject matter will be described in conjunction with these embodiments, it will be understood that they are not intended to limit the subject matter to these embodiments. On the contrary, the subject matter described herein is intended to cover alternatives, modifications and equivalents, which may be included within the spirit and scope as defined by the appended claims. In some embodiments, all or portions of the electronic computing devices, units, and components described herein are implemented in hardware, a combination of hardware and firmware, a combination of hardware and computer-executable instructions, or the like. Furthermore, in the following description, numerous specific details are set forth in order to provide a thorough understanding of the subject matter. However, some embodiments may be practiced without these specific details. In other instances, well-known methods, procedures, objects, and circuits have not been described in detail as not to unnecessarily obscure aspects of the subject matter.

Notation and Nomenclature

Unless specifically stated otherwise as apparent from the following discussions, it is appreciated that throughout the present Description of Embodiments, discussions utilizing terms such as "receiving," "accessing," "determining," "using," "generating," "storing," "correlating," "comparing," or the like, often (but not always) refer to the actions and processes of a computer system or similar electronic computing device. The electronic computing device manipulates and transforms data represented as physical (electronic) quantities within the electronic computing device's processors, registers, and/or memories into other data similarly represented as physical quantities within the electronic computing device's memories, registers and/or other such information storage, processing, transmission, or/or display components of the electronic computing device or other electronic computing device(s).

Overview of Discussion

Example units, systems, and methods for determining the moisture content of a harvested crop are described herein. Discussion begins with description of components of, and operations performed by, a combine harvester in accordance with various embodiments. A discussion of an extendable moisture content sensor in accordance with various embodiments follows. Discussion then turns to description of components of a moisture content sensing system in accordance with various embodiments. Finally, there is a discussion of methods of determining the moisture content of clean grain and a harvested crop in accordance with various embodiments.

Example Integrated Field-Portable Device

Figure 1A:
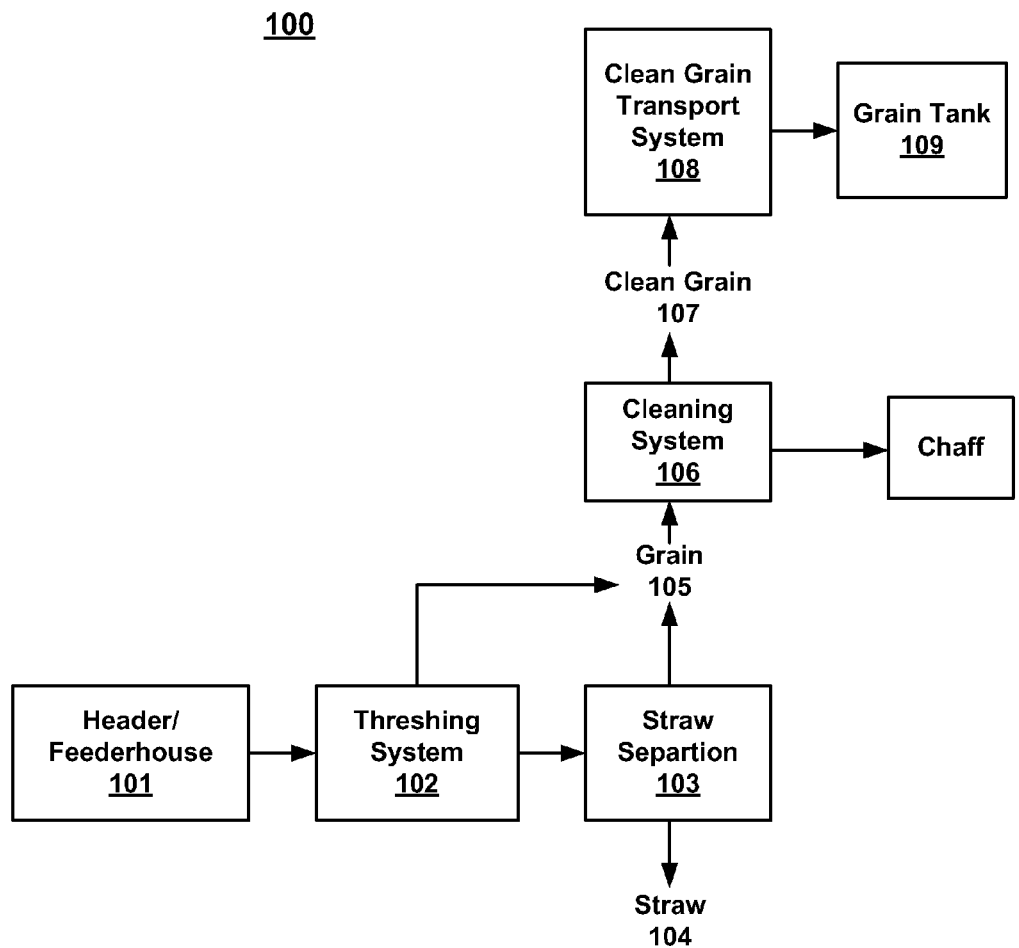
FIG. 1A is a diagram of components and operations performed by a combine harvester in accordance with an embodiment.

FIG. 1A is a block diagram of components and operations performed by a combine harvester 100 in accordance with an embodiment. For the following discussion, combine harvester 100 will herein be described as a "combine." Furthermore, the following discussion will describe the harvesting of a grain such as wheat. However, it is noted that embodiments of the present technology are not limited to grain harvesting alone and can be used to measure the moisture content of other harvested crops as well. Typically, combines comprise a header/feederhouse 101. The header gathers and cuts crops such as corn, wheat, soybeans, etc. and conveys the crops up through a feederhouse via conveyor belt, or a chain elevator. Typically, different headers are used in the harvesting of different types of crops. The crop then enters the threshing system 102 where the grains are separated from the wheat stalks. In the threshing system, a rotating cylinder rubs the grain against concave screens or drums. Most of the grain, as well as some chaff, falls through screens and is conveyed to the cleaning system 106, also referred to as a "chaffer." The larger material such as the grain stalks are conveyed to the straw separation component 103. A typical straw separation component moves back and forth and allows any grain which may remain in the straw to be separated out and sent to cleaning system 106. The straw remaining is ejected as straw 104 from the back of combine 100. A typical cleaning system 106 comprises a series of screens which shake the grain and blow air across it. This separates the heavier grain 105, which fall through the screens, from the lighter chaff which is also ejected from the rear of combine 100. As a result, clean grain 107 is output from cleaning system 106 and is largely free of extraneous plant material. The clean grain 107 is then gathered at cleaning system 106 and conveyed via clean grain transport system 108 to a grain tank 109. From there, the clean grain 107 can off-loaded from combine 100.

Figure 1B:
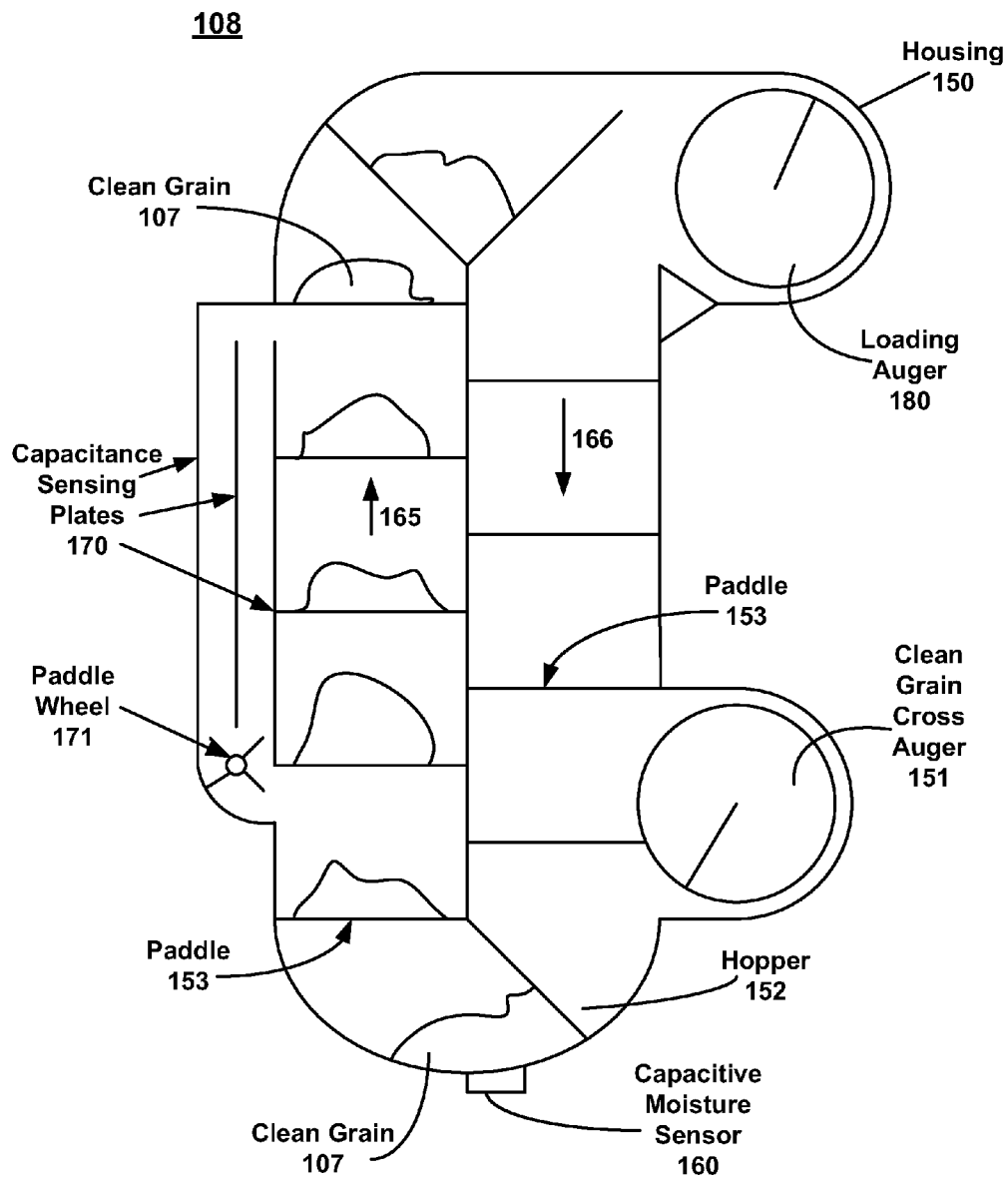
FIG. 1B is a diagram of an example clean grain elevator in accordance with an embodiment.

FIG. 1B is a diagram of an example clean grain elevator (e.g., clean grain transport system 108) in accordance with an embodiment. In FIG. 1B, clean grain transport system 108 comprises a housing 150. Clean grain 107 which has been separated from chaff by cleaning system 106 is gathered by clean grain cross auger 151 and conveyed to a hopper 152. Typically, a chain-driven system uses paddles 153 to lift the clean grain 107 in the direction indicated by arrow 165 up to the top of clean grain transport system 108 where it is gathered by loading auger 180 which conveys clean grain 107 to grain tank 109. The paddles 153 then return to hopper 152 in the direction indicated by arrow 166. While not shown in FIG. 1B, many times a mass flow sensor is a component disposed in clean grain transport system 108. There are a variety of methods for monitoring the mass flow of the harvested crop such as impact sensors, radiation sensors, photoelectric sensors, or a paddle wheel.

As described above, the measurement of the moisture content of a harvested crop is important in precision agriculture applications. Often, capacitance is used to measure the moisture content of a crop. Typically, the clean grain acts as a dielectric material which passes over a capacitive moisture sensor 160 shown in FIG. 1B.

As an alternative, many manufacturers use a capacitive sensing system which is disposed on the side of the grain elevator. As shown in FIG. 1B, some clean grain 107 can fall through an opening in the grain elevator to a region between capacitive plates 170. The moisture content of the clean grain 107 is measured because the clean grain 107 used as a dielectric material between capacitive plates 170. Often, a paddle wheel 171 is disposed below the capacitive plates 170 and turns at a speed which ensures that the space between capacitive plates 170 is filled with clean grain 107. The clean grain 107 then is returned to the grain elevator where it can be conveyed by paddles 153 to the top of the clean grain transport system 108.

Extendable Moisture Content Sensor

Figure 2A:
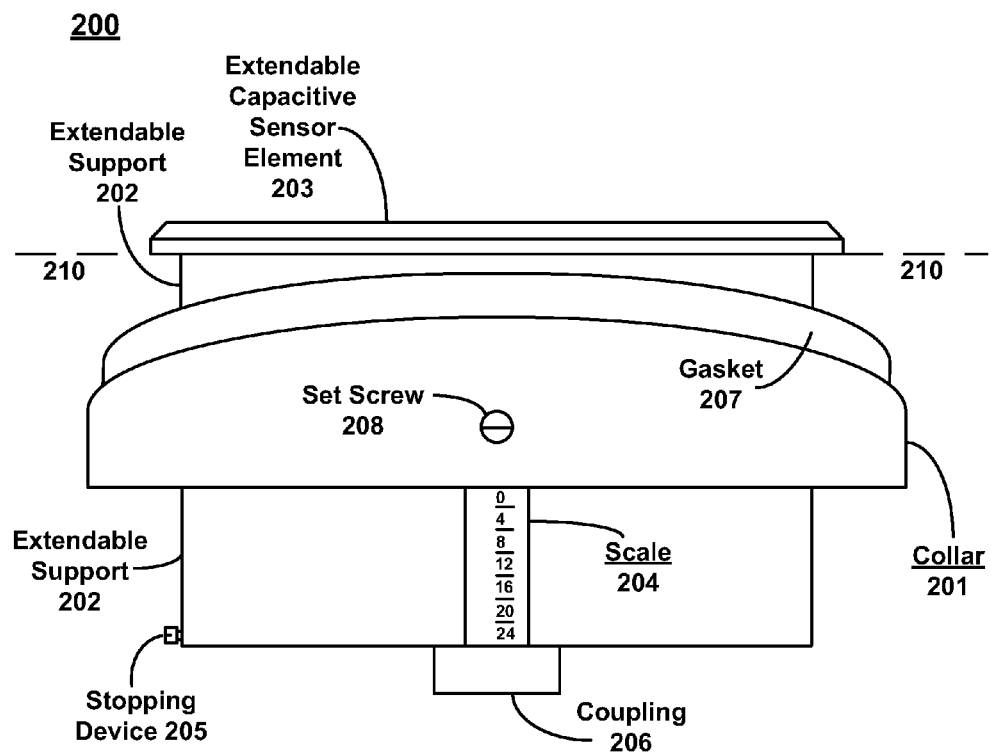
FIG. 2A shows a side elevation view of an extendable moisture content sensor in accordance with an embodiment.
Figure 2B:
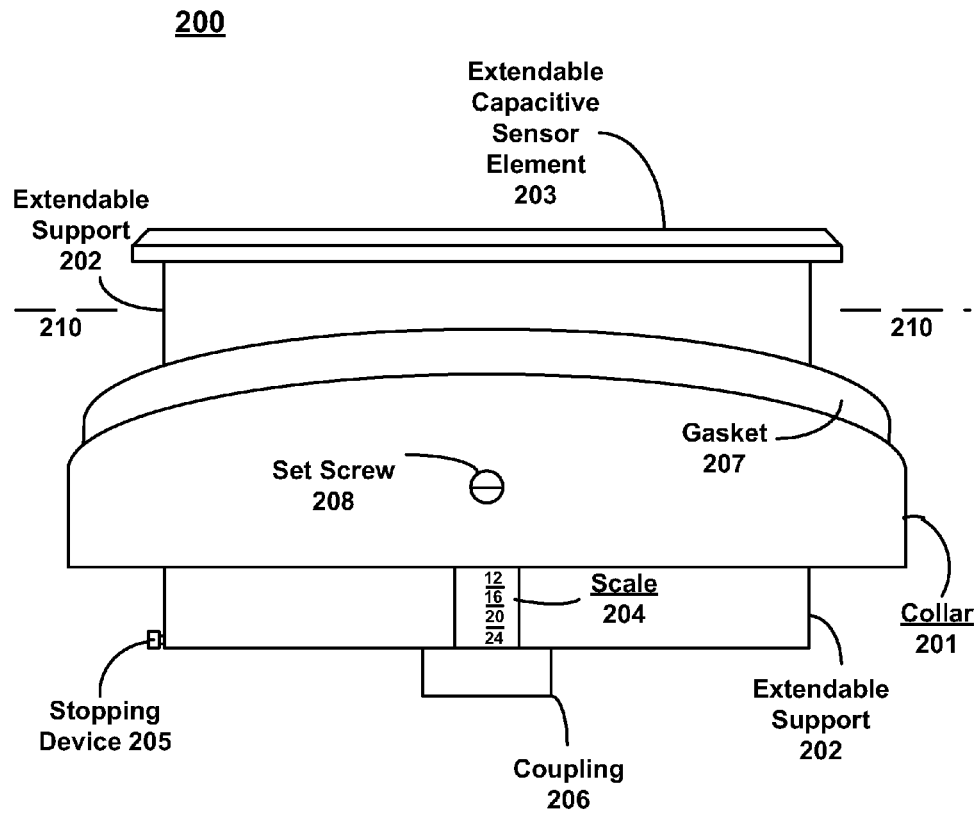
FIG. 2B shows a side elevation view of an extendable moisture content sensor in accordance with an embodiment.

FIGS. 2A and 2B show side elevation views of an extendable moisture content sensor 200 in accordance with an embodiment. In FIG. 2A, extendable moisture content sensor 200 is shown in a retracted position while in FIG. 2B extendable moisture content sensor 200 is shown in an extended position. It is noted that the principle of measuring the moisture content of grain based upon a capacitance reading is known in the art. In FIG. 2A, extendable moisture content sensor 200 comprises a collar 201 which is configured to mechanically coupled with housing 150 of clean grain transport system 108. It is noted that extendable moisture content sensor 200 can be coupled in a variety of positions within clean grain transport system 108 in accordance with various embodiments. In one embodiment, extendable moisture content sensor 200 is coupled with an access door (not shown) which provides access to hopper 152. Extendable moisture content sensor 200 further comprises an extendable support 202 which extends through collar 201. At one end of extendable support 202 is an extendable capacitive sensor element 203 which is used to determine the moisture content of a harvested crop. As shown in FIG. 2A, extendable support 202 is in a retracted position at which extendable capacitive sensor element 203 is disposed adjacent to, but not within, a collection of a harvested crop. In other words, when extendable moisture content sensor 200 is coupled with housing 150, the inside edge of housing 150 is understood to be indicated by dashed lines 210. Thus, when a harvested crop such as clean grain 107 collects in hopper 152, extendable capacitive sensor element 203 does not extend into clean grain 107 but is disposed beneath it.

Also shown in FIG. 2A is a scale 204. A user of extendable moisture content sensor 200 can use scale 204 to determine how far extendable capacitive sensor element 203 extends into the clean grain 107 which has collected at the bottom of hopper 152 prior to being lifted by paddles 153. Because extendable support 202 is shown in a fully retracted position in FIG. 2A, scale 204 reads 0 which indicates that it does not extend into clean grain 107. In contrast, in FIG. 2B extendable moisture content sensor 200 is shown in an extended position. In this instance, scale 204 indicates that extendable capacitive sensor element 203 extends 12 mm into clean grain 107. It is noted that the indication of the distance which extendable capacitive sensor element 203 extends into the flow path of clean grain transport system 108 can be expressed in different units such as inches, centimeters, etc, or as numerical units (e.g., 0, 1, 2, etc.) in accordance with various embodiments.

In FIGS. 2A and 2B, a stopping device 205 is shown. In one embodiment, stopping device 205 is coupled with extendable support 202 and prevents pushing extendable support 202 so far into collar 201 that it disengages from collar 201 and enters into clean grain transport system 108. As shown in FIGS. 2A and 2B, in one embodiment stopping device 205 comprises a screw which prevents pushing extendable support 202 past collar 201. FIGS. 2A and 2B also show coupling 206 which comprises coupling 206 which provides an electrical and communicative interface with other components such as computer system 600 of FIG. 6 and CAN bus 550 of FIG. 5.

Also shown in FIGS. 2A and 2B are a gasket 207. Gasket 207 prevents clean grain 107, or other harvested crops, from falling out of clean grain transport system 108 when extendable moisture content sensor 200 is coupled with, for example, housing 150. Also shown in FIGS. 2A and 2B are a set screw 208. In accordance with various embodiments, set screw 208 applies mechanical pressure upon extendable support 202 and prevents extension or retraction of extendable support 202 when sufficiently tightened. In one embodiment, holes (not shown) are drilled into the sides of extendable support 202 at pre-determined positions so that extendable capacitive sensor element 203 is disposed within the clean grain 107 collected above it at a height indicated by scale 204. In one embodiment, set screw 208 is spring loaded and a user can simply pull it out, raise extendable support 202 to a desired height, and release set screw 208 which will then be pushed into one of the holes and hold extendable support 202 at the desired height. In one embodiment, extendable support 202 and collar 201 are threaded and extendable support 202 is raised or retracted by twisting it relative to collar 201. The holes in the side of extendable support 202 are array diagonally so that when extendable support 202 is raised to a desired height indicated by scale 204, one of the holes in extendable support 202 is aligned with set screw 208.

Figure 2C:
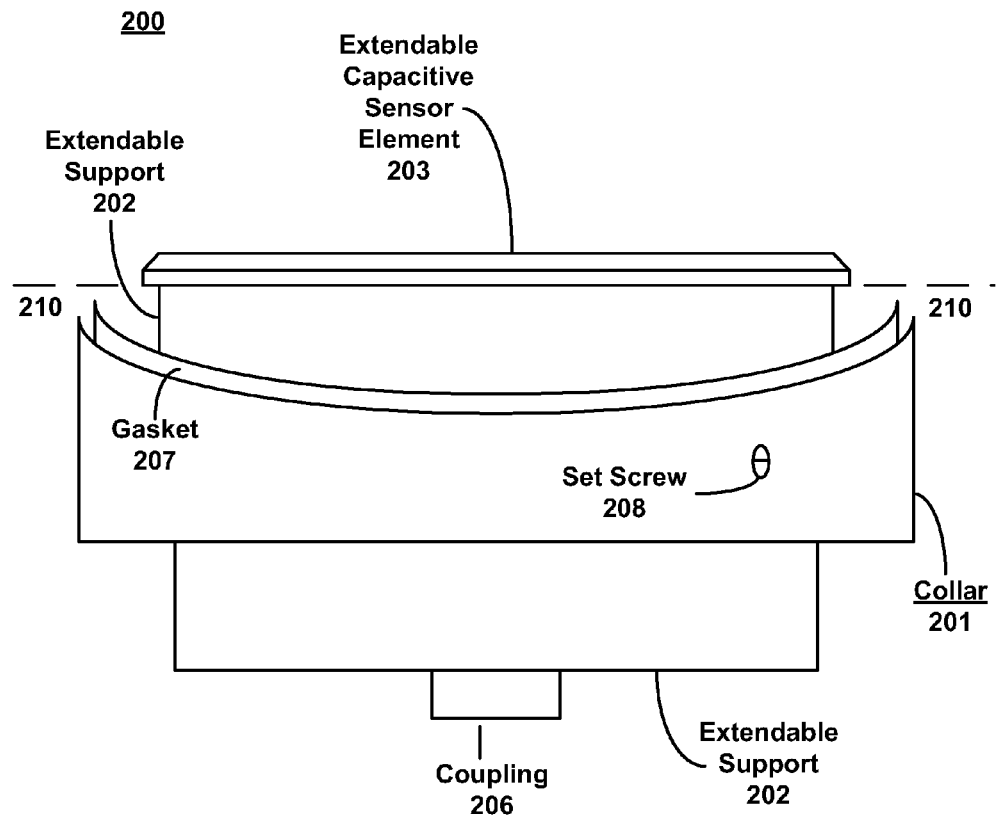
FIG. 2C shows a front elevation view of an extendable moisture content sensor in accordance with an embodiment.
Figure 2D:
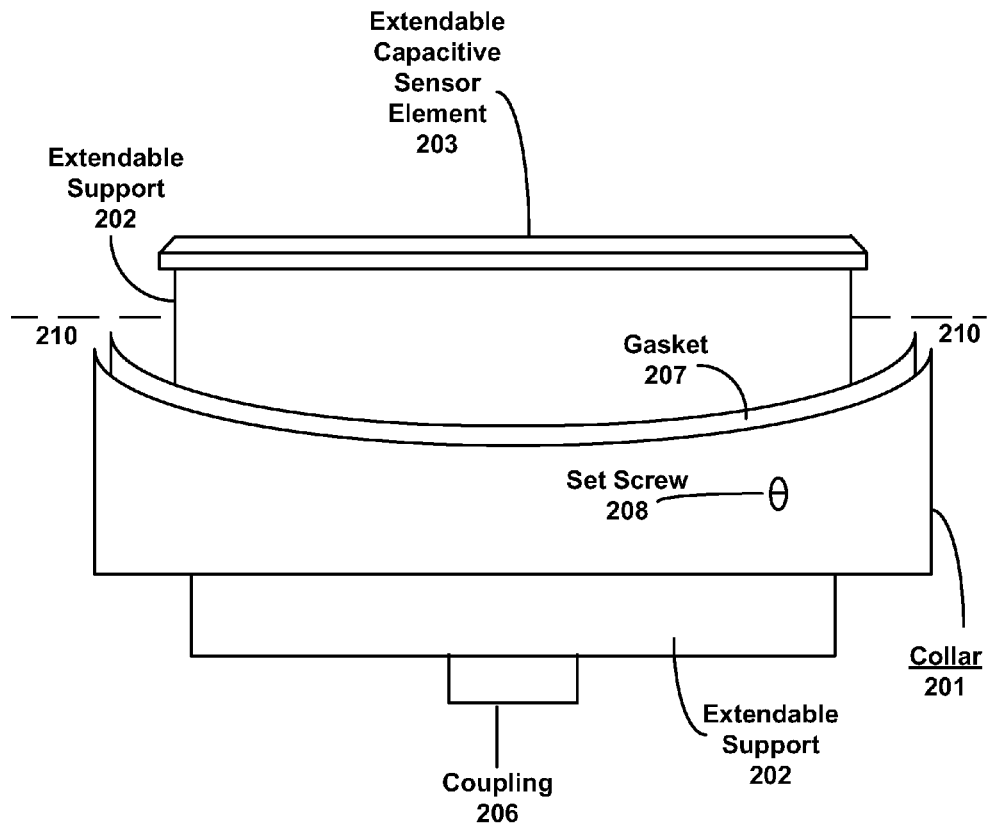
FIG. 2D shows a front elevation view of an extendable moisture content sensor in accordance with an embodiment.

FIGS. 2C and 2D show front elevation views of extendable moisture content sensor 200 in retracted and extended positions respectively in accordance with an embodiment. As shown in FIGS. 2C and 2D, in one embodiment collar 201 has a curved top surface which contacts the bottom of hopper 152. This permits collar 201 to more closely match the contours of whatever surface it is in contact with. However, in other embodiments, collar 201 can exhibit other contours including a flat surface and be coupled with non-matching contours as well. Again, dashed lines 210 indicate the interior surface of hopper 152 and show that, in the retracted position shown in FIG. 2C, extendable capacitive sensor element 203 does not extend into clean grain 107 collected above it, but instead is disposed below or adjacent to clean grain 107. In FIG. 2D, extendable capacitive sensor element 203 is raised above the interior surface of hopper 152 and is now disposed at least partially within clean grain 107 which is collected above extendable moisture content sensor 200 during operation of clean grain transport system 108.

In accordance with various embodiments, one advantage of using extendable capacitive sensor element 203 is that an accumulation of mud over the top of extendable capacitive sensor element 203 is less likely to occur. This in turn prevents degrading of the monitoring of the moisture content of whatever crop is being harvested. In accordance with various embodiments, a farmer can raise capacitive sensor element 203 using extendable support 202 so that it is above the level of accumulating dirt, mud, and plant/grain matter. Additionally, by raising extendable capacitive sensor element 203 above a flush, or nearly flush, mounting relative to the interior surface of hopper 152, the flow 310 of clean grain 107, shown as material 301, tends to physically remove accumulating material from around extendable capacitive sensor element 203. In one embodiment, a farmer can operate extendable moisture content sensor 200 in a retracted position until he notices a build-up of mud and other material around extendable capacitive sensor element 203. At that time, rather than having to repeatedly clean mud away from extendable capacitive sensor element 203, he can simply move it to an extended position using extendable support 202. As a result, the farmer can continue harvesting without having to stop periodically and clean extendable capacitive sensor element 203. An additional benefit is that the farmer can be more confident that accurate measurements of the moisture content of clean grain 107 are being recorded.

Figure 3A:
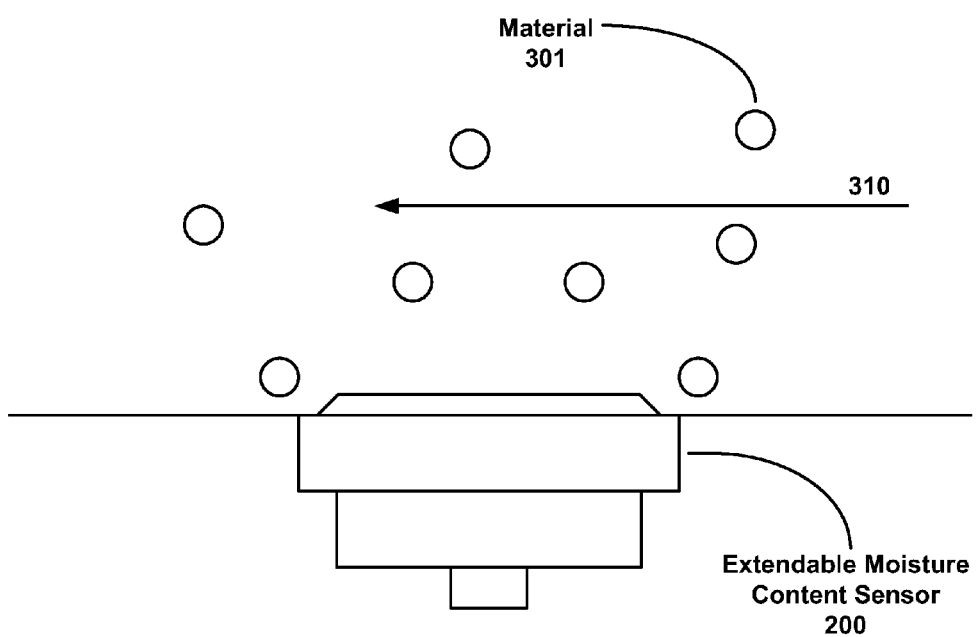
FIG. 3A shows the operation of an example extendable capacitive sensor element in accordance with an embodiment.
Figure 3B:
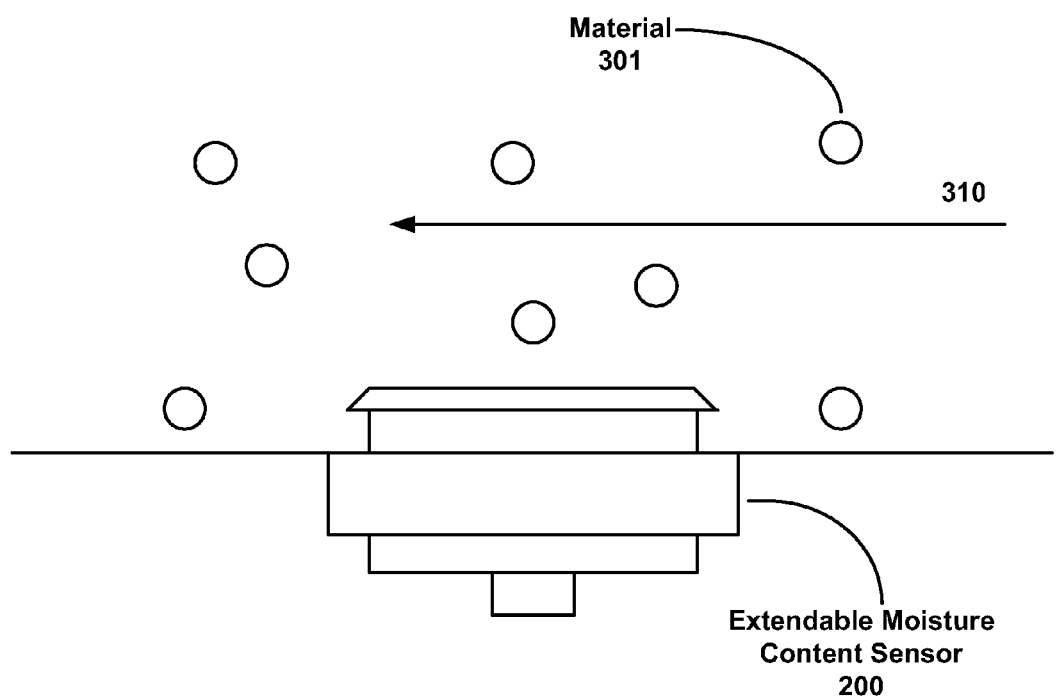
FIG. 3B shows the operation of an example extendable capacitive sensor element in accordance with an embodiment.

FIGS. 3A and 3B show operation of extendable moisture content sensor 200 in accordance with various embodiments. It is noted that by moving extendable capacitive sensor element 203 farther away from collar in the moisture content reading (e.g., apparent moisture content reading 515 of FIG. 5) of clean grain 107 even though the actual moisture content has not changed. In accordance with various embodiments, data table 400 of FIG. 4 stores correction values which are applied to apparent moisture content reading 515 by microprocessor 502 to derive moisture content reading 521. In one embodiment, measurements are made which record how capacitance varies based upon whether extendable support 202, and thus extendable capacitive sensor element 203, is in a retracted position as shown in FIGS. 2A and 2C, or in an extended position as shown in FIGS. 2B and 2D. A model of the variation in observed capacitance is created which permits factoring in a correction value to the apparent moisture content reading 515 detected by extendable capacitive sensor element 203 based upon the positioning of extendable support 202.

With reference now to FIG. 3A, extendable moisture content sensor 200 is shown in a retracted position. In one embodiment, a controlled moisture content material (e.g., material 301 of FIGS. 3A and 3B) is disposed above extendable capacitive sensor element 203. For purpose of illustration, material 301 is assumed to have a uniform controlled moisture content of 12%. A first reading of the capacitance with extendable moisture content sensor 200 in a retracted position as shown in FIG. 3A is recorded. Keeping the same material 301, with a moisture content of 12%, extendable support 202 can be moved to dispose extendable capacitive sensor element 203 at a second position within material 301 as shown in FIG. 3B. A second reading of the capacitance with extendable moisture content sensor 200 in an extended position is then recorded. Typically, the apparent moisture content of material 301 will drop when extendable support 202 is moved from a retracted position (e.g., in FIG. 3A) to an extended one (e.g., in FIG. 3B). By taking these measurements with a controlled moisture content material, a model of the variation in capacitance measured by extendable moisture content sensor 200 is based solely upon the positioning of extendable support 202. Using this information, a plurality of compensation values are generated which account for this variation in capacitance and are stored in data table 400 of FIG. 4. As will be discussed in greater detail below, microprocessor 502 of FIG. 5 uses these compensation values when generating a moisture content reading of clean grain 107.

Figure 4:
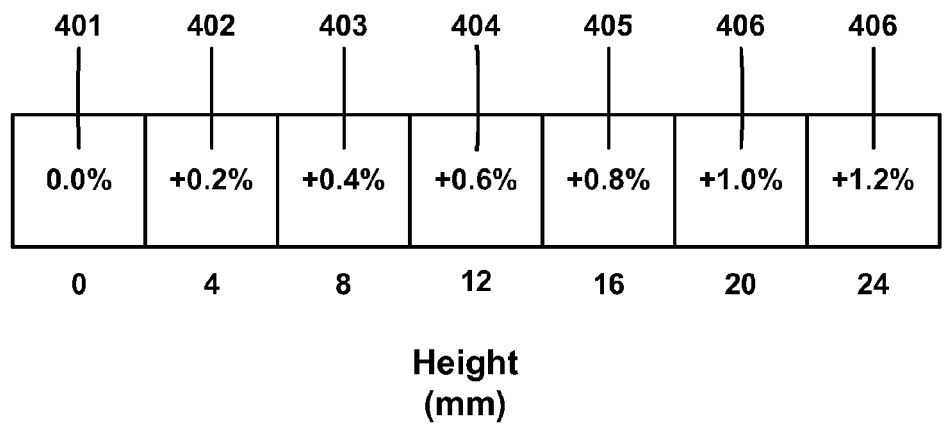
FIG. 4 shows an example data table used in accordance with an embodiment.

Referring now to FIG. 4, data table 400 shows a variety of compensation values which are added to apparent moisture content reading 515 in accordance with various embodiments. In FIG. 4, a variety of height measurements are shown. These correlate to the readings which are taken using scale 204 and indicate the height that extendable capacitive sensor element 203 is disposed above the interior surface of hopper 152. As shown in FIG. 4, when extendable support 202 is in a fully retracted position, as shown for example in FIG. 2A, scale 204 reads 0 mm. As shown in FIG. 4, in one embodiment, compensation value 401 indicates that no compensation is added to apparent moisture content reading 515 when extendable support 202 is not extended into material 301. If a user moves extendable support 202 such that extendable capacitive sensor element 203 now extends 24 mm into material 301, an apparent drop in the moisture content of material 301 of 1.2% was recorded. As a result, the compensation value 406 indicates that a compensation of 1.2% is applied to apparent moisture content reading 515 to derive the moisture content reading 521 generated by microprocessor 502 of FIG. 5. In one embodiment, a linear interpolation is made to generate the compensation values for the variation in capacitance when extendable support 202 is moved to other positions. Other methods for performing interpolation are possible and well-known. Linear interpolation is appropriate for an embodiment of this application. For example, compensation values are calculated based upon the capacitance readings from extendable moisture content sensor 200 when extendable capacitive sensor element 203 extends 0 mm and extends 24 mm into material 301. A linear interpolation is performed to calculate the compensation values when extendable capacitive sensor element 203 extends other distances (e.g., 4 mm, 8 mm, 12 mm, 16 mm, and 20 mm) into material 301. Thus, the compensation values for the 4, 8, 12, 16, and 20 mm positions of extendable support 202 (e.g., compensation values 402, 403, 404, and 405 respectively) were generated as a result of a linear interpolation. In another embodiment, discreet compensation values are generated based upon measuring the variation in capacitance which is observed when extendable support 202 is moved to each position (e.g., the, 8, 12, 16, and 20 mm positions of extendable support 202). Thus, compensation values 401, 402, 403, 404, 405, and 406 can be derived based upon observed data.

Figure 5:
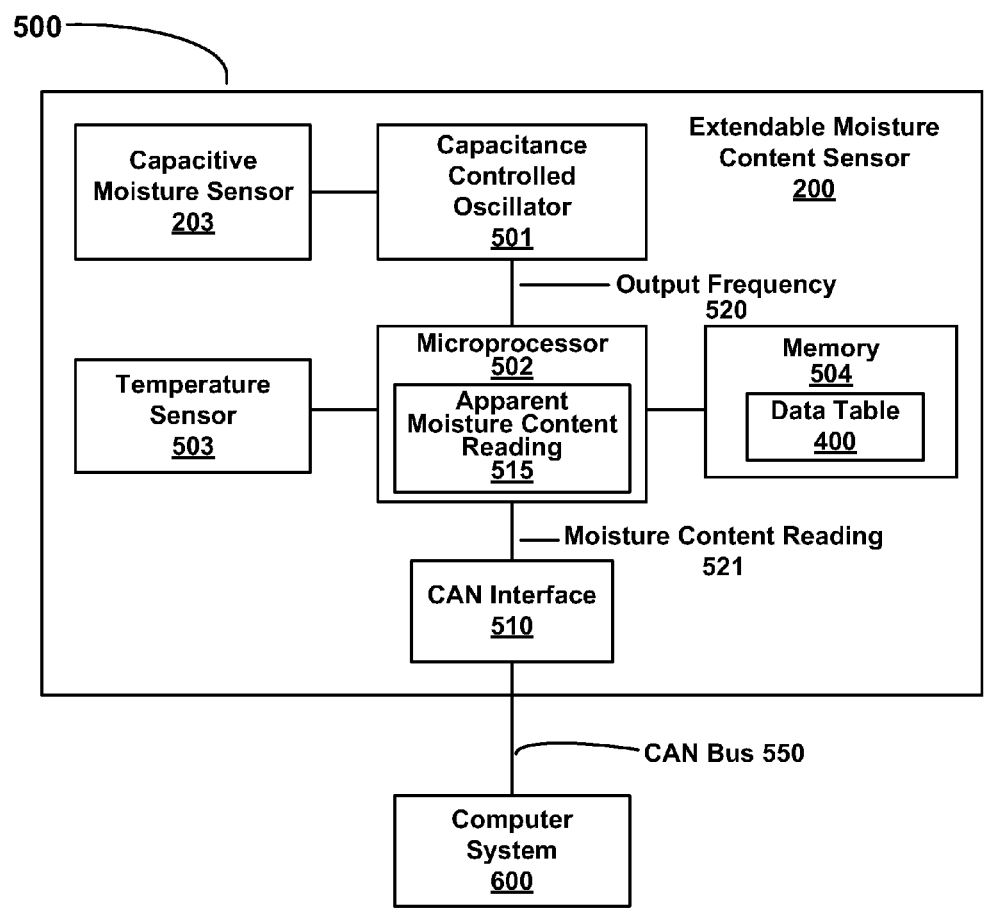
FIG. 5 shows an example moisture content sensing system in accordance with various embodiments.

With reference now to FIG. 5, components of an example moisture content sensing system 500 in accordance with various embodiments are shown. In FIG. 5, moisture content sensing system 500 comprises extendable capacitive sensor element 203 which is communicatively coupled with a capacitance controlled oscillator 501. Capacitance controlled oscillator 501 is in turn communicatively coupled with microprocessor 502. In operation, a capacitance signal from extendable capacitive sensor element 203 is converted by capacitance controlled oscillator 501 to an output frequency 520. Microprocessor 502 is configured to receive output frequency 520 and derive an apparent moisture content reading 515 of clean grain 107 based upon output frequency 520. In one embodiment, a temperature sensor 503 is also coupled with microprocessor 502. This allows accounting for variations in capacitance readings based upon the ambient temperature.

Figure 6:
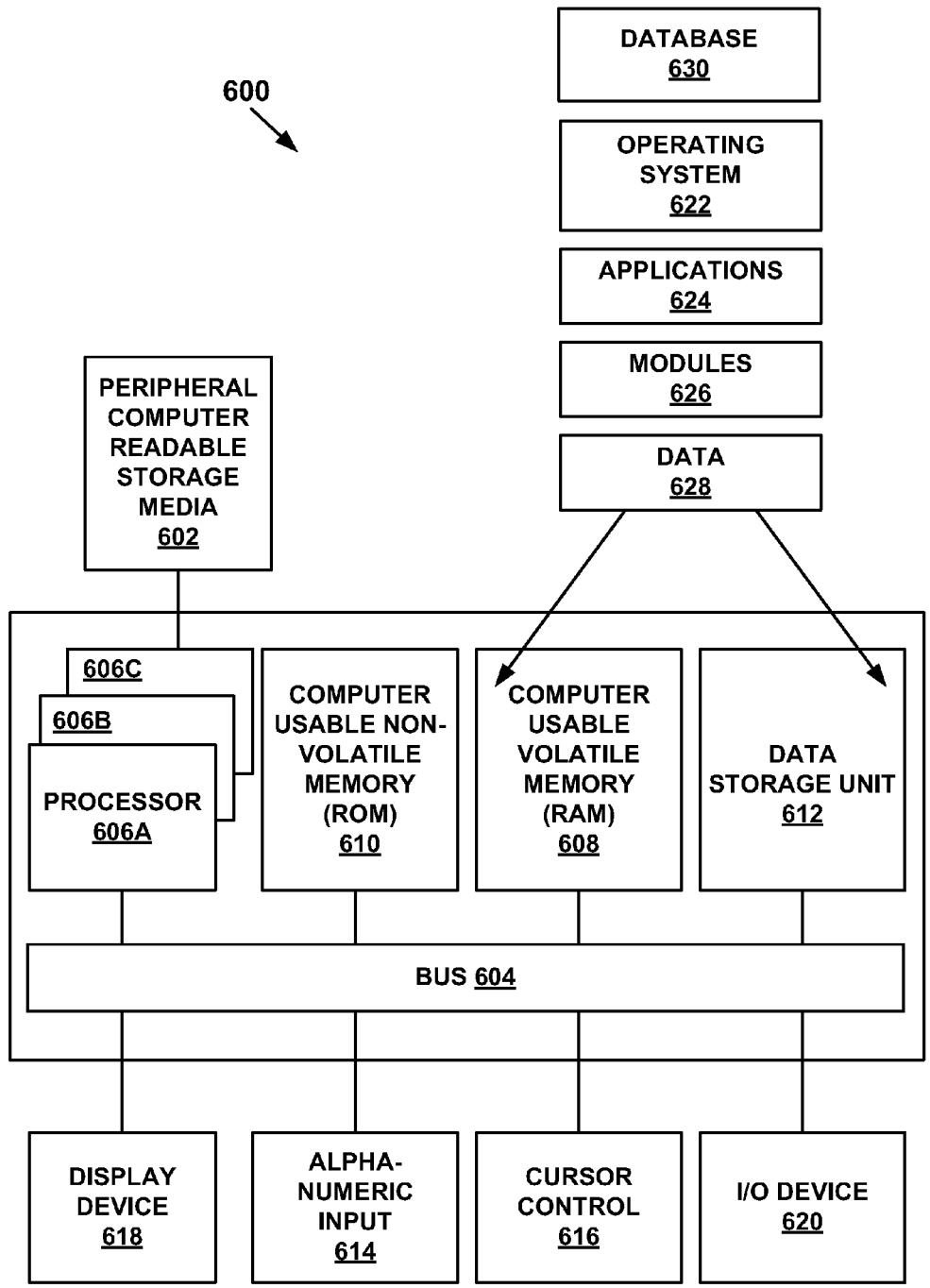
FIG. 6 illustrates a block diagram of an example computer system with which or upon which various embodiments may be implemented.

In FIG. 5, microprocessor 502 is communicatively coupled with a Controller Area Network (CAN) interface 510 which facilitates communication between moisture content sensing system 500 and, for example, computer system 600 of FIG. 6. Thus, microprocessor 502 can send moisture content reading to computer system 600. In the embodiment of FIG. 5, a memory 504 coupled with microprocessor 502 stores a data table 400. In accordance with various embodiments, memory 504 can be a persistent memory device, a non-persistent memory device, a removable data storage device, a tangible computer-readable medium, a database, or the like. In one embodiment, capacitance controlled oscillator 501, microprocessor 502, temperature sensor 503, memory 504, and CAN interface 510 are components disposed upon extendable moisture content sensor 200 (e.g., disposed upon a printed circuit board, or integrated circuit). In another embodiment, various components described above with reference to FIG. 5 may be discreet components, or integrated into other devices such as computer system 600 of FIG. 6.

In one embodiment, a farmer reads scale 204 to determine the height of extendable capacitive sensor element 203 with respect to the interior surface of hopper 152. This indicates how far extendable capacitive sensor element 203 extends into clean grain 107. The farmer enters this information using computer system 600 which is then sent to microprocessor 502. Microprocessor 502 then accesses data table 400 and determines what correction value is to be added to apparent moisture content reading 515 which is derived based upon the output frequency 520 received from capacitance controlled oscillator 501. By adding the correction value based upon the indication of the distance extendable capacitive sensor element 203 extends into clean grain 107, microprocessor 502 compensates for the change in the capacitance caused by moving the position of extendable capacitive sensor element 503. As a result of applying a correction value to apparent moisture content reading 515, moisture content reading 521 is generated which conveys the actual moisture content of clean grain 107. In other words, the apparent moisture content of clean grain 107 is adjusted to account for the position of extendable capacitive sensor element 203 relative to clean grain 107. While the present embodiment cites a data table 400 which stores correction values based upon the position of extendable support 202 and extendable capacitive sensor element 203, embodiments of the present technology are not limited to a data table alone. In one embodiment, microprocessor 502 is configured to implement an algorithm which applies a correction value to the moisture content reading derived based upon the output frequency 520 received from capacitance controlled oscillator 501, when the sensor is not covered by grain, for example, after the initial installation or after any adjustment of the height of the sensor.

Example Computer System Environment

With reference now to FIG. 6, all or portions of some embodiments described herein are composed of computer-readable and computer-executable instructions that reside, for example, in computer-usable/computer-readable storage media of a computer system. That is, FIG. 6 illustrates one example of a type of computer (computer system 600) that can be used in accordance with or to implement various embodiments which are discussed herein. It is appreciated that computer system 600 of FIG. 6 is only an example and that embodiments as described herein can operate on or within a number of different computer systems including, but not limited to, general purpose networked computer systems, embedded computer systems, server devices, various intermediate devices/nodes, stand alone computer systems, hand-held computer systems, multi-media devices, and the like. In one embodiment, computer system 600 comprises a display device/controller for an agricultural vehicle. Computer system 600 of FIG. 6 is well adapted to having peripheral computer-readable storage media 602 such as, for example, a floppy disk, a compact disc, digital versatile disc, universal serial bus "thumb" drive, removable memory card, and the like coupled thereto.

System 600 of FIG. 6 includes an address/data bus 604 for communicating information, and a processor 606A coupled to bus 604 for processing information and instructions. As depicted in FIG. 6, system 600 is also well suited to a multi-processor environment in which a plurality of processors 606A, 606B, and 606C are present. Conversely, system 600 is also well suited to having a single processor such as, for example, processor 606A. Processors 606A, 606B, and 606C may be any of various types of microprocessors. System 600 also includes data storage features such as a computer usable volatile memory 608, e.g., random access memory (RAM), coupled to bus 604 for storing information and instructions for processors 606A, 606B, and 606C. System 600 also includes computer usable non-volatile memory 610, e.g., read only memory (ROM), coupled to bus 604 for storing static information and instructions for processors 606A, 606B, and 606C. Also present in system 600 is a data storage unit 612 (e.g., a magnetic or optical disk and disk drive) coupled to bus 604 for storing information and instructions. System 600 also includes an optional alphanumeric input device 614 including alphanumeric and function keys coupled to bus 604 for communicating information and command selections to processor 606A or processors 606A, 606B, and 606C. System 600 also includes an optional cursor control device 616 coupled to bus 604 for communicating user input information and command selections to processor 606A or processors 606A, 606B, and 606C. In one embodiment, system 600 also includes an optional display device 618 coupled to bus 604 for displaying information.

Referring still to FIG. 6, optional display device 618 of FIG. 6 may be a liquid crystal device, cathode ray tube, plasma display device or other display device suitable for creating graphic images and alphanumeric characters recognizable to a user. In one embodiment, display device 618 comprises a touch-screen assembly configured to detect the location of a touch on, or proximate to, the surface of display device. There are numerous implementations of a touch screen assembly known in the art which can be utilized as implementations of display device 618 including, but not limited to, resistive touch screen assemblies, capacitive touch screen assemblies, infrared touch screen assemblies, surface acoustic wave touch screen assemblies, and the like. Optional cursor control device 616 allows the computer user to dynamically signal the movement of a visible symbol (cursor) on a display screen of display device 618 and indicate user selections of selectable items displayed on display device 618. Many implementations of cursor control device 616 are known in the art including a trackball, mouse, touch pad, joystick or special keys on alphanumeric input device 614 capable of signaling movement of a given direction or manner of displacement. Alternatively, it will be appreciated that a cursor can be directed and/or activated via input from alphanumeric input device 614 using special keys and key sequence commands. System 600 is also well suited to having a cursor directed by other means such as, for example, voice commands. System 600 also includes an I/O device 620 for coupling system 600 with external entities. For example, in one embodiment, I/O device 620 is a modem for enabling wired or wireless communications between system 600 and an external network such as, but not limited to, the Internet.

Referring still to FIG. 6, various other components are depicted for system 600. Specifically, when present, an operating system 622, applications 624, modules 626, data 628, and database 630 are shown as typically residing in one or some combination of computer usable volatile memory 608 (e.g., RAM), computer usable non-volatile memory 610 (e.g., ROM), and data storage unit 612. In some embodiments, all or portions of various embodiments described herein are stored, for example, as an application 624 and/or module 626 in memory locations within volatile memory 608, computer-readable storage media within data storage unit 612, peripheral computer-readable storage media 602, and/or other tangible computer readable storage media.

FIG. 7 is a flowchart of an example method 700 of determining the moisture content of a harvested crop in accordance with one or more embodiments. In operation 710, an indication of a distance an extendable capacitive sensor element extends into a collection of a harvested crop is received. In one embodiment, a farmer uses computer system 600 to enter the distance extendable capacitive sensor element 203 extends into clean grain 107. Using this information, microprocessor accesses the appropriate compensation values to apply to moisture content data received from capacitance controlled oscillator 501.

In operation 720, a frequency signal is received. As discussed above, in one embodiment capacitance controlled oscillator 501 generates output frequency 520 based upon the capacitance signal received from extendable capacitive sensor element 203. Based upon the frequency received, microprocessor 502 is configured to generate apparent moisture content reading 515 of clean grain 107. However, depending upon the height extendable capacitive sensor element 203 extends into clean grain 107, apparent moisture content reading 515 may or may not accurately convey the actual moisture content of clean grain 107.

In operation 730, the moisture content of the collection of the harvested crop is determined based upon the indication of the distance and the frequency signal. In one embodiment, microprocessor 502 combines one of compensation values 401-406 with apparent moisture content reading 515 to generate moisture content reading 521 which accounts for the variation in capacitance exhibited when extendable capacitive sensor element 203 is moved from a retracted position to an extended position.

FIG. 8 is a flowchart of an example method 800 of determining the moisture content of clean grain in accordance with one or more embodiments. In operation 810, at least one data table is generated indicating a correction to a moisture content reading of a controlled moisture content material generated by an extendable capacitive sensor element disposed upon an extendable support. As discussed above, data table 400 comprises at least compensation value which indicates how to adjust apparent moisture content reading 515 to account for the variation in capacitance exhibited when extendable capacitive sensor element 203 is moved from a retracted position to an extended position.

In operation 820, an indication of a distance the extendable capacitive sensor element extends into a collection of clean grain is received. Again, a farmer reads scale 204 to determine how far extendable capacitive sensor element 203 extends into clean grain 107. This information is entered via computer system 600 and is used by microprocessor 502 to determine the appropriate compensation value to apply to apparent moisture content reading 515.

In operation 830, a frequency signal is received. Again, based upon the capacitance signal received from extendable capacitive sensor element 203, capacitance controlled oscillator 501 varies output frequency 520. Output frequency 520 is received by microprocessor 502 and is used to generate apparent moisture content reading 515 of clean grain 107.

In operation 840, a moisture content of the collection of clean grain is determined based upon the indication of the distance and the frequency signal. Using the compensation value selected based upon the indication of how far extendable capacitive sensor element 203 extends into clean grain 107, microprocessor 502 makes a correction to apparent moisture content reading 515 of clean grain 107 and generates moisture content reading 521.

FIG. 9 is a flowchart of a method 900 for measuring moisture content of a harvested crop in accordance with various embodiments. In operation 910, an extendable capacitive sensor element is extended into a collection of clean grain within a clean grain transport system of a combine. As discussed above, in accordance with various embodiments extendable capacitive sensor element 203 can be moved from a retracted position of clean grain transport system 108, as shown for example in FIG. 3A, to an extended position, as shown for example in FIG. 3B, wherein it extends into a collection of clean grain (e.g., represented as material 301 of FIGS. 3A and 3B).

In operation 920, based on a distance the extendable capacitive sensor extends into the collection of clean grain and a frequency signal received from the extendable capacitive sensor element, a moisture content of the collection of clean grain is determined In accordance with one embodiment, based upon the capacitance signal generated by extendable capacitive sensor element 203, output frequency 520 is generated which indicates an apparent moisture content 515 of the clean grain. A farmer or operator of computer system 600 can also enter the distance extendable capacitive sensor element 203 extends into clean grain (e.g., 301 of FIGS. 3A and 3B). Based upon this value, a correction value (e.g., 401-406 of FIG. 4) is selected. This correction value is applied to the apparent moisture content reading to derive the actual moisture content of the clean grain.

Embodiments of the present technology are thus described. While the present technology has been described in particular embodiments, it should be appreciated that the present technology should not be construed as limited to these embodiments alone, but rather construed according to the following claims.

What is claimed is:

1. A moisture content sensing system comprising:
   a collar mechanically coupled with a clean grain transport system;
   an extendable support extending through said collar and having an extendable capacitive sensor element disposed at one end, said extendable support configured to be located at a first position in which said extendable capacitive sensor element is disposed adjacent to clean grain conveyed by said clean grain transport system and to be located at a second position wherein said extendable capacitive sensor element is disposed at least partially within said clean grain conveyed by said clean grain transport system; and
   a processor configured to adjust a moisture content reading of the clean grain based upon an indication of a distance said extendable capacitive sensor element extends into the clean grain and a respective frequency signal from said extendable capacitive sensor element when located at at least one of said first position and said second position.

2. The extendable moisture content sensing system of claim 1 further comprising:
   a scale which is configured to indicate the distance said extendable capacitive sensor element extends into the clean grain.

3. The extendable moisture content sensing system of claim 2 further comprising:
   a capacitance controlled oscillator communicatively coupled with said extendable capacitive sensor element and with said processor and configured to vary an output frequency based upon a capacitance signal received from said extendable capacitive sensor element.

4. The extendable moisture content sensing system of claim 1 further comprising:
   a non-transitory memory device comprising a data table accessed by said processor which stores a correction value to be applied to said moisture content reading based upon said distance.

5. The extendable moisture content sensing system of claim 4 wherein said data table of said non-transitory memory device comprises a plurality of compensation values which are derived using interpolation to describe a variation in said moisture content reading based upon the position of said extendable capacitive sensor element.

6. The extendable moisture content sensing system of claim 1 further comprising:
   a stopping device configured to prevent said extendable support from entering entirely into the clean grain.

7. A method of determining the moisture content of a harvested crop, said method comprising:
   receiving an indication of a distance an extendable capacitive sensor element extends into a collection of a harvested crop;
   receiving a frequency signal; and
   generating a moisture content reading of said harvested crop based upon said indication of said distance and said frequency signal.

8. The method of claim 7 further comprising:
   using a scale which is disposed proximate to an extendable collar upon which said extendable capacitive sensor element is disposed to determine said distance said extendable capacitive sensor element extends into said collection of said harvested crop.

9. The method of claim 7 further comprising:
   receiving a capacitance signal from said extendable capacitive sensor element by a capacitance controlled oscillator communicatively coupled with said extendable capacitive sensor element; and
   generating said frequency signal based upon said capacitance signal which indicates said moisture content reading.

10. The method of claim 7 further comprising:
    accessing a data table which stores a correction value to be applied to said moisture content reading based upon said indication.

11. The method of claim 10 further comprising:
    generating an interpolation which describes a variation in said moisture content reading based upon the position of said extendable capacitive sensor element into a controlled moisture content material; and
    storing said interpolation in said data table.

12. A method for determining the moisture content of clean grain, said method comprising:
    accessing a data table having a plurality of data points and interpolating a correction for making an adjustment of a moisture content reading of a controlled moisture content material generated by an extendable capacitive sensor element disposed upon an extendable support;
    receiving an indication of a distance said extendable capacitive sensor element extends into a collection of clean grain;
    receiving a frequency signal; and
    determining a moisture content of said collection of clean grain based upon said indication of said distance and said frequency signal.

13. The method of claim 12 further comprising:
    generating a first moisture content reading based upon a signal from said extendable capacitive sensor element when said extendable capacitive sensor element is disposed at a first distance into said controlled moisture content material;
    generating a second moisture content reading based upon a second signal from said extendable capacitive sensor element when said extendable capacitive sensor element is disposed at a second distance into said controlled moisture content material; and
    generating said data table which indicates a variation in said moisture content reading based upon the position of said extendable capacitive sensor element at said first distance into said controlled moisture content material and said second distance into said controlled moisture content material.

14. The method of claim 13 further comprising:
generating an interpolation which describes a variation in said moisture content reading based upon the position of said extendable capacitive sensor element into said controlled moisture content material; and
storing said interpolation in said data table.

15. The method of claim 14 wherein said determining said moisture content further comprises:
receiving a capacitance signal from said extendable capacitive sensor element by a capacitance controlled oscillator communicatively coupled with said extendable capacitive sensor element; and
generating said frequency signal based upon said capacitance signal received from said extendable capacitive sensor element.

16. The method of claim 15 further comprising:
receiving said frequency signal when said extendable capacitive sensor element is extended into said collection of clean grain;
determining said moisture content reading of said collection of clean grain based upon said frequency signal;
accessing said data table to determine said correction to be applied to said moisture content reading based upon said indication of said distance; and
applying said correction to said moisture content reading to generate an adjusted moisture content reading.

17. A method for measuring moisture content of a harvested crop comprising:
extending an extendable capacitive sensor element into a collection of clean grain within a clean grain transport system of a combine; and
based on a distance said extendable capacitive sensor extends into said collection of clean grain and a frequency signal received from said extendable capacitive sensor element, determining a moisture content of said collection of clean grain.

18. The method of claim 17 further comprising:
determining a first moisture content reading of said clean grain based upon said frequency signal;
accessing a data table which stores a correction value to be applied to said moisture content reading based upon said distance said extendable capacitive sensor element extends into said collection of clean grain; and
applying said correction value to said first moisture content reading to derive said moisture content of said collection of clean grain.

19. The method of claim 18 further comprising:
generating an interpolation which describes a variation in capacitance measured by said extendable capacitive sensor element based upon the position of said extendable capacitive sensor element into a controlled moisture content material; and
storing said linear interpolation in said data table.

* * * * *